United States Patent [19]

Liao et al.

[11] Patent Number: 5,728,796
[45] Date of Patent: Mar. 17, 1998

[54] PROCESS TO REACT EPOXIDE-CONTAINING COMPOUNDS AND ALIPHATIC ALCOHOLS

[75] Inventors: Zeng K. Liao; James L. Bertram, both of Lake Jackson, Tex.

[73] Assignee: The Dow Chemical Company, Midland, Mich.

[21] Appl. No.: 652,580

[22] Filed: May 31, 1996

Related U.S. Application Data

[63] Continuation-in-part of Ser. No. 171,054, Dec. 21, 1993, abandoned.

[51] Int. Cl.$^6$ .......................... C07C 41/03; C07C 43/13
[52] U.S. Cl. ................... 528/88; 528/110; 528/361; 528/408; 525/407; 525/523; 549/516; 568/607; 568/611; 568/618; 568/619; 568/620; 568/660; 568/662; 568/664; 568/670; 568/679; 568/680; 568/811; 568/822; 568/831; 568/867; 568/678
[58] Field of Search ............... 525/407, 523; 549/516; 568/607, 611, 618, 619, 620, 660, 662, 664, 670, 679, 680, 811, 822, 831, 867, 678, 866, 902; 528/110, 88, 361, 408

[56] References Cited

U.S. PATENT DOCUMENTS

| | | | |
|---|---|---|---|
| 4,543,430 | 9/1985 | Falgoux et al. | 568/678 |
| 4,707,535 | 11/1987 | Koleske | 528/110 |
| 5,117,010 | 5/1992 | Cheng | 549/516 |
| 5,134,239 | 7/1992 | Bertram et al. | 546/112 |
| 5,169,473 | 12/1992 | Bertram et al. | 156/307.4 |
| 5,245,048 | 9/1993 | Rolfe et al. | 549/516 |
| 5,342,903 | 8/1994 | Wolleb et al. | 525/407 |

FOREIGN PATENT DOCUMENTS

| | | |
|---|---|---|
| 0 139 042 | 12/1983 | European Pat. Off. . |
| 0 121 260 | 3/1984 | European Pat. Off. . |
| 0 491 529 | 12/1991 | European Pat. Off. . |
| 0 493 916 | 12/1991 | European Pat. Off. . |
| 0 498 504 | 1/1992 | European Pat. Off. . |
| 0 491 529 | 6/1992 | European Pat. Off. . |
| 0 493 916 | 7/1992 | European Pat. Off. . |
| 0 545 576 | 11/1992 | European Pat. Off. . |
| 0 552 864 | 1/1993 | European Pat. Off. . |
| 0 569 331 | 11/1993 | European Pat. Off. . |

OTHER PUBLICATIONS

Chemical Abstracts 98:53239, "Trimethylsilyl Triflate Induced Reaction . . . ", Shirahama et al.
Chemical Abstracts 97:92373,"Trimethylsilyl Triflate in Organic Synthesis", Noyori et al.
1993 Derwent Publication 93–353399/45 Abstract of EP 0 569 331.

*Primary Examiner*—Frederick Krass

[57] ABSTRACT

A process reaction between: (1) a compound that contains one or more epoxide moieties per molecule, and (2) a compound that contains one or more primary aliphatic hydroxyl groups per molecule; is catalyzed by: (3) a catalyst compound containing one or more trifluoromethane-sulfonate moieties and one or more silyl moieties and run at a temperature of no more than 130° C., such that the catalyst preferably catalyzes reaction at the primary aliphatic hydroxyl group, so that the resulting resin does not gel.

14 Claims, No Drawings

PROCESS TO REACT EPOXIDE-CONTAINING COMPOUNDS AND ALIPHATIC ALCOHOLS

This is a continuation-in-part of application Ser. No. 08/171,054, filed Dec. 21, 1993 and now abandoned.

The present invention relates to processes to make and react epoxy resins.

It is well known to react compounds which contain epoxy groups with compounds which contain phenolic hydroxyl groups. For instance, low molecular weight epoxy resins can be advanced by reacting the low molecular weight epoxy resin with a bisphenol or a biphenol, such as bisphenol A or resorcinol. An example of the reaction is given in Formula I:

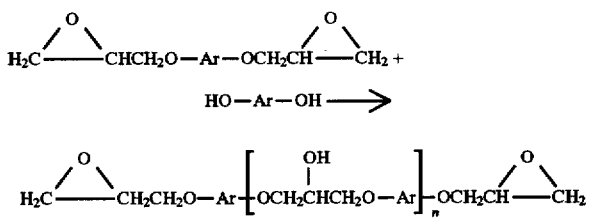

wherein each Ar is an organic moiety containing one or more aromatic rings, which are bonded directly to the oxygen atoms, and n is a number of repeating units greater than zero. The reaction is usually carried out neat (without the use of a solvent other than the reagents themselves) and is usually catalyzed by a base (such as an alkali metal hydroxide, sodium carbonate, and amine) or by a quaternary ammonium salt. See, for example, 6 *Encyclopedia Poly. Sci. & Eng., Epoxy Resins*, 322, 328–331 (J. Wiley & Sons 1986) and H. Lee & K. Neville, *Handbook of Epoxy Resins* 2–9 (McGraw-Hill 1967). Similar reactions are used to make diglycidyl ethers of bisphenols, through the reaction of the bisphenol with epihalohydrin in the presence of a catalyst amount of base.

In some instances, it is desirable to react an epoxy-containing compound with an aliphatic diol or polyol (such as 1,4-butanediol) rather than with a bisphenol or biphenol. For instance, the resin containing aliphatic moieties might have improved flexibility, toughness, and/or weatherability, depending upon the aliphatic diol and the epoxy-containing compound that was used. For example, the reaction might be as illustrated in Formula II(a) or (b):

Unfortunately, the reaction of epoxy-containing compounds with aliphatic diols has proven very difficult to perform controllably. The aliphatic hydroxyl group is substantially less reactive than phenolic hydroxyl groups, so that stronger reaction conditions are needed. Under the reaction conditions, undesirable side reactions can occur. First, epoxy groups can polymerize with each other by ordinary step-growth polymerization methods, as with poly-alkylene oxides. Second, the advancement product contains pendant secondary aliphatic hydroxyl groups (see Formula 2). Epoxy groups can react with those secondary hydroxyl groups under the same conditions that they react with the aliphatic diol to form branched or cross-linked structures. The branched or cross-linked structures form gels or high viscosity mixtures, both of which are undesirable. This difficulty is discussed in H. Lee & K. Neville, *Handbook of Epoxy Resins*, at 2–16 to 2–18 (McGraw-Hill, Inc. 1967).

U.S. Pat. No. 4,707,535 teaches that aliphatic moieties can be incorporated into cured systems by reacting excess aliphatic diol with polyepoxide in the presence of a sulfonic acid compound to create a low molecular weight adduct, which is then cured with ordinary epoxy resins. This approach does not provide a method to prevent undesirable side reactions.

European Patent Publication 0 493 916 A2 (published Jul. 8, 1992) teaches reactions of epoxy resins and aliphatic diols in the presence of certain metal salts of trifluoromethanesulfonic acid at temperatures of 160° C. to 205° C. This approach does not provide a method to prevent undesirable side reactions.

What is needed is a process to react an epoxy-containing compound with a primary aliphatic alcohol, which selectively encourages the desired reaction over either the epoxy—epoxy reaction or the reaction with secondary aliphatic alcohols.

The present invention is a process to react:

(1) a compound that contains one or more epoxide moieties per molecule, and (2) a compound that contains one or more aliphatic hydroxyl groups per molecule, characterized in that:

(a) the aliphatic hydroxyl groups in component (2) are bonded to a primary carbon atom;

(b) the reaction is carried out in the presence of a catalytic amount of a trifluoromethanesulfonic acid or a derivative thereof; and (c) the reaction is carried out at a temperature of no more than 130° C.

In the process, alcohols react either: (1) with epihalohydrins to make aliphatic epoxy resins, or (2) with epoxy resins to make advanced epoxy resins. Preferably, the reactions can

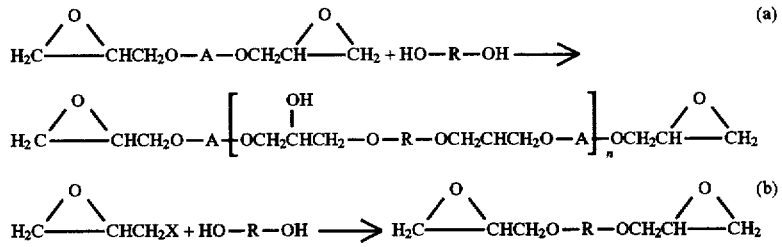

wherein A is an aromatic- or aliphatic-containing moiety, R is an organic group having aliphatic moieties bonded to the oxygen atoms, X is a halogen atom, and n is a number of repeating units which averages greater than zero.

be carried out without a solvent, at relatively low temperatures, with few side reactions. The resulting epoxy resins can be used for ordinary purposes, such as coatings, adhesives, and composite matrices.

The present invention uses an alcohol that contains one or more primary aliphatic hydroxyl groups. "Primary aliphatic hydroxyl group" means a hydroxyl group which is bonded to a primary aliphatic carbon atom. For example, the moiety is represented by the formula —$CH_2OH$ or —$CX_2OH$, wherein X is a halogen atom. The moiety is preferably represented by the formula —$CH_2OH$. The compound preferably contains at least about two primary aliphatic hydroxyl groups linked by a central organic moiety. It preferably contains no more than about 10 hydroxyl groups, more preferably no more than about 4 hydroxyl groups, and most preferably no more than about 2 hydroxyl groups. The compound may optionally contain phenolic hydroxyl groups, secondary hyroxyl groups, or tertiary hydroxyl groups as well, but such hydroxyl groups are preferably minimized. Preferably 51 to 100 percent of the hydroxyl groups are primary aliphatic hydroxyl groups; more preferably, 75 to 100 percent are primary aliphatic hydroxyl groups; and most preferably about 100 percent are primary aliphatic hydroxyl groups.

The compound is preferably represented by Formula III:

Formula III

wherein:

Q is an aliphatic or aromatic-aliphatic moiety, m is a number of hydroxyl groups greater than or equal to 1, and at least one of the hydroxyl groups is bonded to a primary aliphatic carbon atom.

The central moiety (Q) is preferably a saturated or unsaturated aliphatic or cycloaliphatic moiety, and is more preferably a saturated aliphatic or cycloaliphatic moiety. It preferably contains at least 2 carbon atoms, more preferably at least 3 carbon atoms and most preferably at least 4 carbon atoms. The maximum number of carbon atoms is not critical and is limited primarily by practical considerations. Preferably, it contains no more than 200 carbon atoms, more preferably no more than 20 carbon atoms, and most preferably no more than 8 carbon atoms. Q may also contain hetero atoms, such as oxygen, sulfur, nitrogen, phosphorus or silicon. For instance, Q may be a polyetherpolyol moiety or an oxyalkylated phenolic compound or a hydroxy-functional polyester. Q may also contain substituents that do not interfere with the reaction, such as alkoxy or aryloxy moieties and halogen atoms. Substituents that react with epoxy resins, such as carboxylic acids, and hydrides, amine groups, and amide groups most preferably are not present.

Q is preferably chosen so that the alcohol is liquid or is soluble in the epoxy compound under reaction conditions. Examples of suitable alcohols include: ethanol, propanol, butanol, cyclohexanol, fatty alcohols, propylene oxide polyether polyol, ethylene oxide polyether polyol, butylene oxide polyether polyol, glycerol, erythritol, trimethylolpropane, pentaerythritol, sorbitol, glucose, or oxyalkylated phenolic compounds, such as the oxyalkylated bisphenols described in Bowditch, U.S. Pat. No. 4,507,461

(Mar. 26, 1975) and in Anderson, U.S. Pat. No. 5,212,262 (May 18, 1993). More preferred examples include 1,2-ethylene glycol; diethylene glycol; triethylene glycol, tetraethylene glycol; 1,3-propanediol; 1,4-butanediol; 1,3-butanediol; 1,6-hexanediol; 1,5-hexanediol; 1,4-cyclohexanedi-methanol; 1,7-heptanediol; 1,8-octanediol; neopentyl glycol, trimethylolethane and trimethylolpropane.

The present invention also uses a compound containing one or more epoxide groups. (For the purposes of the present invention the term "epoxide group" refers to a 3-membered oxirane ring.) The epoxide-containing compound may optionally contain a single epoxide group, such as a glycidyl acrylate, a glycidyl methacrylate, an alkylene oxide or an epihalohydrin (for instance, epichlorohydrin, epibromohydrin, or epiiodohydrin). The epihalohydrin is preferably epichlorohydrin. The epoxide-containing compound is preferably a polyepoxide (containing on average more than one epoxide group per molecule).

The polyepoxide preferably contains on average at least about two epoxide groups. It preferably contains on average no more than 10 epoxide groups, more preferably no more than 4 epoxide groups, and most preferably, no more than 2.1 epoxide groups. Its epoxide equivalent weight (EEW) is preferably at least 100, more preferably at least 150 and most preferably at least 170. Its epoxide equivalent weight is preferably no more than 1000, more preferably no more than 350, and most preferably no more than 200.

The polyepoxide is preferably a poly(glycidyl ether), poly(glycidyl ester) or a poly(glycidyl amine). It is more preferably a poly(glycidyl ether). It is preferably represented by any one of Formulae IV(a)–(b):

Formula IV

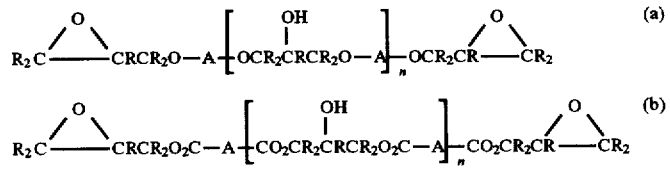

wherein:

each "A" is independently a divalent organic moiety, each "R" is independently a hydrogen atom, a lower (about $C_1$–$C_6$) alkyl group, a lower alkoxide group, an aryloxide group, or a halogen, "n" represents a number of repeating units that averages between 0 and 50.

The polyepoxide is most preferably represented by Formula 4(a). "n" preferably averages 0 to 2, more preferably 0 to 1 and most preferably 0 to 0.5. Each "A" is preferably aliphatic, aromatic, or aromatic-aliphatic. "R" moieties are preferably not linked to make cyclic structures. Each "R" is preferably hydrogen.

Examples of suitable polyepoxides are described in: Sheih, U.S. Pat. No. 4,596,861 (Jun. 24, 1986); Heinemeyer, EPO Publ. 0,414,160 A2 (Feb. 27, 1991); and 6 Encyclopedia of Polymer Sci. & Eng., "Epoxy Resins" at 324–331 (J. Wiley & Sons 1986). Examples of suitable polyglycidyl ethers include polyglycidyl ethers of novolac resins, trisphenol resins, aliphatic diols, and polyetherpolyols. Examples of suitable polyglycidyl esters are derived from hexahydrophthalic acid or from polymers of glycidyl acrylate or glycidyl methacrylate. Examples of suitable polyglycidyl amine include N,N,N,N-tetraglycidylmethylenedianiline. Other examples of useful polyepoxides include siloxanecontaining poly(glycidyl ethers) and poly(glycidyl esters), such as those described in Zahir et al., U.S. Pat. No. 4,954,580 (Sep. 4, 1990); Liao et al., U.S. Pat. No. 5,188,903 (Feb. 23, 1993); and Liao et al., U.S. Pat. No. 5,206,312 (Apr. 27, 1993). Preferred examples of polyepoxides include diglycidyl ethers and partially advanced diglycidyl ethers of bisphenol A, bisphenol F, resorcinol and dihydroquinone. Suitable polyepoxides are commercially available from The Dow Chemical Company, for instance under the trademark D.E.R.* 330, D.E.R.* 332, D.E.R.* 383, D.E.R.* 331, and D.E.R.* 317 (*registered trademark of The Dow Chemical Company). The polyepoxide is most preferably a diglycidyl ether of bisphenol A.

The reaction mixture may optionally contain other advancing or curing agents, such as bisphenols, biphenols, amine-containing compounds, amide-containing compounds and anhydrides. Biphenols and bisphenols are preferred advancing and curing agents. Most preferably, no other reagents are present.

The equivalent ratio of hydroxyl-containing compounds to epoxide-containing compounds is preferably between 1:99 and 99:1. The equivalent ratio is more preferably between 5:95 and 95:5.

In one preferred embodiment in which the reaction makes cured or high-molecular weight resins, the reaction mixture contains about equal equivalents of hydroxyl-containing compounds and epoxide-containing compounds. The equivalent ratio of hydroxyl-containing compounds to epoxide-containing compounds is preferably between 35:65 and 65:35; more preferably between 40:60 and 60:40; and most preferably between 45:55 and 55:45.

In another preferred embodiment in which the reaction makes an epoxy-terminated resin or adduct, the reaction mixture contains a stoichiometric excess of epoxide-containing compounds over hydroxyl-containing compounds. The equivalent ratio of hydroxyl-containing compounds to epoxide-containing compounds is more preferably less than 40:60 and most preferably less than 35:65. This embodiment is preferably used in the reaction of epihalohydrin with a hydroxyl-containing compound.

In a third preferred embodiment in which the reaction makes a hydroxyl-terminated resin or adduct, the reaction mixture contains a stoichiometric excess of hydroxyl-containing compounds. The equivalent ratio of hydroxyl-containing compounds to epoxide-containing compounds is more preferably greater than 60:40 and most preferably greater than 65:35.

The reaction is catalyzed by a catalytic amount of trifluoromethanesulfonic acid or a derivative thereof. The catalyst contains one or more trifluoromethanesulfonate moieties and counter-moieties, such as hydrogen or another group which does not interfere with the reactivity of the catalyst.

The catalyst is preferably represented by any of the following Formulae (a)–(c):

Formula V (a)–(c)

(X)(Z)     (a)

CM–(XZ)$_a$     (b)

CM–(SiR$_2$—X)$_b$     (c)

wherein each "X" is a trifluorosulfonate moiety, each "Z" is a counter-moiety, "CM" is a central organic moiety that does not interfere with the reaction, "a" is a number of pendant catalyst moieties bonded to a central organic moiety and is greater than 1, and "b" is a number of pendant catalyst moieties bonded to the central organic moiety and is greater than 1. The catalyst is more preferably represented by Formula V(a) or (b), and is most preferably represented by Formula V(a).

Examples of suitable counter-moieties (Z) for the trifluoromethanesulfonate moiety include hydrogen atoms, silyl moieties, ammonium moieties, phosphonium moieties, sulfonium moieties, and metal cations. The counter-moiety is preferably not an alkali metal cation and more preferably not a metal cation. Each counter-moiety (Z) is preferably a hydrogen atom or a silyl moiety. The silyl moiety is preferably represented by Formula VI:

Formula VI

—Si(R')$_3$ wherein each R' is a non-electron-withdrawing moiety that: (1) does not interfere with the reaction; and (2) has an electronegativity lower than the electron-withdrawing group, so that an ionic or polar covalent bond is formed.

Each non-electron-withdrawing moiety (R') is preferably a hydrogen atom, an organic group or a silyl group; is more preferably a hydrogen atom or an organic group; and is most preferably an organic group. Each organic group independently is preferably an aliphatic or aromatic group, more preferably an alkyl or aromatic group, and most preferably an alkyl group. Each preferably contains no more than about 20 carbon atoms, more preferably no more than about 10 carbon atoms, more highly preferably no more than about 6 carbon atoms, and most preferably no more than about 4 carbon atoms. Each contains at least about 1 carbon atom. Highly preferred examples of organic groups include phenyl groups, methyl groups, ethyl groups, propyl groups, and butyl groups.

Examples of suitable organosilyl moieties include: trialkylsilyl moieties, triphenyl silyl moieties, dialkylphenylsilyl moieties and hydrodialkyl-silyl moieties.

Examples of suitable catalysts include: trimethylsilyl trifluoromethylsulfonate, triethylsilyl trifluoromethylsulfonate, triisopropylsilyl trifluoromethylsulfonate, t-butyldiphenylsilyl trifluoromethylsulfonate, t-butyldimethylsilyl trifluoromethylsulfonate, ammonium trifluoromethylsulfonate, tetramethylammonium trifluoromethylsulfonate, phosphonium trifluoromethylsulfonate, tetramethylphosphonium trifluoromethylsulfonate, trifluoromethanesulfonic acid, and resins containing pendant moieties of such catalysts. The most preferred catalysts are trifluoromethanesulfonic acid and its organosilyl derivatives.

The quantity of catalyst is not critical as long as there is sufficient catalyst to catalyze the reaction. The concentration of catalyst is preferably between 0.1 ppm and 10 weight percent (based on the total weight of epoxide-containing and hydroxy-containing compound). The concentration is preferably at least about 50 ppm and more preferably at least about 100 ppm. It is preferably no more than about 10,000 ppm and more preferably no more than about 5000 ppm. The mixture preferably contains a least about $10^{-7}$ equivalents of catalyst per equivalent of epoxide group, more preferably at least about $4 \times 10^{-6}$ equivalents, and most preferably at least about $8 \times 10^{-6}$ equivalents. The mixture preferably contains no more than about 0.08 equivalents of catalyst per equivalent of epoxide group, more preferably no more than about $8 \times 10^{-3}$ equivalents, and most preferably no more than about $8 \times 10^{-3}$ equivalents.

The reaction mixture may optionally contain solvents (other than the reagents themselves) that do not interfere with the reaction. Solvents preferably do not contain active hydrogen atoms, such as are present on alcohols, phenols, amines, amides and acids. Examples of suitable solvents include ethers, ketones, aromatic compounds, and polar aprotic solvents. Preferably, the reaction mixture contains less than 30 weight percent solvent, more preferably less than 10 weight percent solvent, more highly preferably less than 9 weight percent solvent, and most preferably less than about 1 weight percent solvent. Optimally, the reaction mixture contains essentially no (0 weight percent) solvent.

The reaction temperature should be high enough for the reaction to go forward at a reasonable rate and low enough so that undesirable side reactions are minimized. The reaction temperature is preferably at least about −20° C., more preferably at least about 0° C., more highly preferably at least about 20° C., and most preferably at least about 70° C. The reaction temperature is preferably no more than about 120° C., more preferably no more than about 110° C., and most preferably no more than about 100° C. Temperatures that are too high may encourage undesirable side reactions.

The pressure and the atmosphere are not critical, as long as they do not interfere with the reaction. The pressure should be high enough that the reagents remain intimately admixed throughout the reaction. It is preferably about atmospheric pressure. Examples of suitable atmospheres include air, nitrogen, and noble gases. The reaction may be carried out under vacuum. The reaction preferably takes place with agitation.

The reaction may be run in a continuous or batch fashion. The reaction time is not critical as long as sufficient time is allowed for the reaction to be substantially completed and as long as the reaction is not carried out for so long that substantial side reactions can occur. The reaction time is preferably between about 30 minutes and about 24 hours, more preferably between about 1 and 12 hours, and most preferably between about 3 and 7 hours. Scale up to commercial equipment may shorten those desirable reaction times.

The resulting resins may optionally be treated after the reaction according to known processes. If the epoxy-containing compound was an epihalohydrin, then the product may contain chlorohydrin groups, which can be converted to glycidyl ether groups by reaction with a strong base. Residual catalyst in the reaction product may be neutralized with basic compounds. Other post treatment steps may include ordinary purification such as: washing, filtration and distillation.

The resulting resins may be used for ordinary purposes. Hydroxy-terminated resins can be used as curing agents with isocyanates and anhydrides. Epoxy-terminated compounds can be reacted with known curing agents, such as amines, amides, polyols, polyphenols and polyanhydrides.

The catalyst is selective for reaction of epoxide rings with primary aliphatic hydroxyl groups, rather than with secondary epoxide groups. When all other variables are equal, the reaction rate of primary aliphatic groups is preferably at least about 2 times the rate for secondary aliphatic groups, highly preferably at least about 5 times, and more preferably at least about 10 times, and most preferably at least about 20 times greater.

When the reaction is a reaction of epihalohydrin with an aliphatic-hydroxyl-containing compound, then the reaction preferably has the added advantage of producing a resin with reduced halide content. For instance, the product preferably contains less than 50,000 ppm halide, and more preferably no more than about 10,000 ppm, and most preferably no more than about 5000.

The invention is further illustrated by the following examples.

The following examples are for illustrative purposes only, and should not be taken as limiting the scope of the specification or claims. Unless stated otherwise, all parts and percentages are by weight.

EXAMPLE 1

A mixture containing:

(a) 181.11 grams of diglycidyl ether of bisphenol A having an EEW of 181.11 and an epoxide content of 23.74 percent;

(b) 22.53 grams 1,4-butanediol having a hydroxyl equivalent weight of 45.06; and (c) 0.25 cc of a solution of anhydrous diglyme containing 12.5 weight percent trimethylsilyl-trifluoromethanesulfonate (available from Aldrich Chemical Co.), was mixed under nitrogen atmosphere. The mixture had an epoxide content of 21.06 percent. (Epoxide content is the weight percent of the epoxide rings—containing 2 carbon atoms, 3 hydrogen atoms and an oxygen atom measured by titration with perchloric acid and tetramethylammonium bromide mixture). The mixture was heated to 100° C. and reacted for 3 hours. The mixture yielded an advanced epoxy resin-butanediol adduct with an epoxide content of 13.78 percent.

EXAMPLE 2

The reaction of Example 1 was repeated except that the epoxy resin was 150.2 grams of phenyl glycidyl ether having an EEW of 150.2. The reaction mixture had an epoxide content of 25.10 percent. The reaction mixture was heated for 7 hours at 100° C. The resulting advanced resin had an epoxide content of 13.29 percent.

EXAMPLE 3

The reaction of Example 1 was repeated except that, in place of the epoxy resin, 186 grams of epichlorohydrin was substituted and the reaction was carried out at 800° C. over a period of 5 hours. The epoxide content of the mixture was 38.76 percent at the beginning of the reaction and 29.96 percent at the end of the reaction. This adduct could be converted to the aliphatic diglycidyl ether by reaction with a strong base, such as an alkali metal hydroxide.

EXAMPLE 4

(A) A mixture containing:

(a) 272 grams of diglycidyl ether of bisphenol A having an EEW of 181.11 and an epoxide content of 23.74 percent;

(b) 33.8 grams 1,4-butanediol having a hydroxyl equivalent weight of 45.06; and (c) 0.38 cc of a solution containing 12.5 weight percent triethylsilyl-trifluoromethanesulfonate (available from Aldrich Chemical Co.) dissolved in anhydrous diglyme, was mixed under nitrogen atmosphere. The mixture had an epoxide content of 20.85 percent. The mixture was heated to 100° C. and reacted for 6 hours. The mixture yielded an advanced epoxy resin-butanediol adduct with an epoxide content of 11.53 percent.

(B) To demonstrate that the catalyst did not substantially catalyze epoxide—epoxide reactions, the same reaction was run without butanediol. The reaction mixture had an epoxide content of 23.74 percent. After 7 hours, the epoxide content of the mixture was 23.01. This is not an example of the invention.

(C) To demonstrate that the catalyst was selective for reaction of primary hydroxyl groups, a mixture containing:

(a) 179.15 grams of diglycidyl ether of bisphenol A having an EEW of 179.15;

(b) 112 g of an adduct of phenylglycidyl ether and 1-butanol (which contained 0.5 equivalents of secondary hydroxyl group); and (c) 0.25 cc of a solution containing 12.5 weight percent triethylsilyl-trifluoromethanesulfonate (available from Aldrich Chemical Co.) dissolved in anhydrous diglyme, was mixed and heated to 100° C. After 7 hours, the epoxide content of the mixture changed from 14.78% to 13.98%. The small change indicates that the catalyst was less active for catalyzing epoxide-secondary hydroxyl reactions.

EXAMPLE 5

(A) The reaction of Example 2 was repeated, except that: (1) the catalyst was triethylsilyltrifluoro-methanesulfonate; and (2) the reaction mixture was heated for 5 hours at 100° C. The epoxide content of the reaction mixture was 25.13 percent at the start of the reaction and 12.17 percent at the end of the reaction.

(B) To demonstrate that the catalyst was selective against epoxide—epoxide reactions, the same reaction was run for 7 hours without butanediol. This is not an example of the invention. The epoxide content changed from 28.35 percent to 27.63 percent. The small change indicated that the catalyst was less active for catalyzing epoxide—epoxide reactions.

(C) To demonstrate that the catalyst was selective to primary alcohols, the same reaction was run substituting 122 g of an adduct of phenylglycidyl ether and phenol (which contains 0.5 equivalents of secondary hydroxyl group). This is not an example of the invention. After 7 hours reaction time, the epoxide content went from 15.36 percent to 14.64 percent. The small change indicated that the catalyst was less active for catalyzing epoxide-secondary hydroxyl reactions.

EXAMPLE 6

The reaction in Example 4(A) was repeated, except that 241 g of diglycidyl ester of cyclohexane-1,2-dicarboxylic acid (having an EEW of 160.4) was substituted in place of the diglycidyl ether of bisphenol A. After 4 hours of reaction time, the epoxide content of the mixture went from 22.97 percent to 11.74 percent.

EXAMPLE 7

(A) A 179.1 g quantity of diglycidyl ether of bisphenol A (with an EEW of 181.11) was mixed with 66.91 g of ethylene oxide-capped bisphenol A (having the average structure in Formula VI):

Formula VI

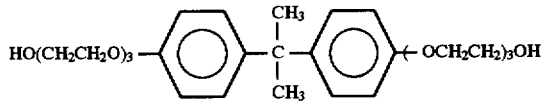

having a hydroxyl equivalent weight of 245.7. A 0.40 cc anhydrous diglyme solution containing 12.5 weight percent triethylsilyl-trifluoromethanesulfonate was added under nitrogen, and the reaction was continued as in Example 1. After 6 hours reaction at 100° C., the epoxide content of the reaction mixture went from 17.39 percent to 13.04 percent. High performance liquid chromatography analysis (HPLC) showed that 83 percent of the ethylene-oxide capped bisphenol A had reacted with epoxide.

(B) The previous reaction is repeated using 0.60 cc of catalyst solution. The mixture had an epoxide content of 17.35 percent at the commencement of the reaction and 12.31 percent after 5 hours reaction time.

EXAMPLE 8

(A) The reaction of Example 4(A) was repeated using as the catalyst 0.45 cc of anhydrous diglyme solution containing 12.5 weight percent triisopropylsilyl-trifluoromethanesulfonate. The epoxide content of the reaction mixture is 20.81 percent at the commencement of the reaction, and 10.61 percent after 7 hours reaction time.

(B) To demonstrate that the catalyst was selective for reaction of primary hydroxyl groups, a mixture containing:

(a) 179.15 grams of diglycidyl ether of bisphenol A having an EEW of 179.15;

(b) 112 g of an adduct of phenylglycidyl ether and 1-butanol (which contained 0.5 equivalents of secondary hydroxyl group); and (c) 0.35 cc of a solution containing 12.5 weight percent triisopropylsilyl-trifluoromethanesulfonate (available from Aldrich Chemical Co.) dissolved in anhydrous diglyme, was reacted as in Example 8(A). The epoxide content of the solution was 14.77 percent at the commencement of the reaction and 13.84 percent after 7 hours reaction time. The small change indicated that the catalyst was less active for catalyzing epoxide-secondary hydroxyl reactions.

EXAMPLE 9

(A) The reaction of Example 8(A) was repeated, using as the catalyst 0.38 cc of an anhydrous diglyme solution containing 12.5 weight percent t-butyldimethylsilyl-trifluoromethanesulfonate. The epoxide content of the reaction mixture is 20.84 percent at the commencement of the reaction, and 10.68 percent after 6 hours reaction time.

(B) To demonstrate that the catalyst was selective for reaction of primary hydroxyl groups, the reaction of Example 8(B) was repeated, using as the catalyst 0.25 cc of an anhydrous diglyme solution containing 12.5 weight percent t-butyldimethylsilyl-trifluoromethanesulfonate. The epoxide content of the solution was 14.81 percent at the commencement of the reaction and 13.61 percent after 7 hours reaction time. The small change indicated that the catalyst was less active for catalyzing epoxide-secondary hydroxyl reactions.

We claim:

1. A process to react:

(1) an epoxide-containing compound that contains one or more epoxide moieties per molecule, and (2) an aliphatic hydroxyl-containing compound that contains one or more aliphatic hydroxyl groups per molecule, characterized in that:

(a) at least one or more of the aliphatic hydroxyl groups in Component (2) are bonded to a primary carbon atom;

(b) the reaction is carried out in the presence of a catalytic amount of a catalyst compound selected from any one of the following formulae:

wherein each "X" is a trifluoromethanesulfonate moiety, each "Z" is a silyl moiety, "CM" is a central organic moiety that does not interfere with the reaction, "a" is the number of pendant catalyst moieties bonded to the central organic moiety and is greater than 1, and "b" is the number of pendant catalyst moieties bonded to the central organic moiety and is greater than 1; and (c) the reaction is carried out at a temperature of no more than 130° C.

2. A process as described in claim 1, wherein the silyl moiety is any of: a trialkylsilyl moiety, a triphenyl silyl moiety, a dialkylphenylsilyl moiety, or a hydrodialkylsilyl moiety, wherein each alkyl group contains 1 to 6 carbon atoms.

3. A process as described in claim 1 wherein the temperature of the reaction is 20° C. to 110° C.

4. A process as described in claim 1 wherein the equivalent ratio of aliphatic hydroxyl-containing compound to epoxide-containing compound is from 40:60 to 60:40.

5. A process as described in claim 1 wherein the equivalent ratio of aliphatic hydroxyl-containing compound to epoxide-containing compound is from 1:99 to 40:60.

6. A process as described in claim 1 wherein the epoxide-containing compound is any of: a glycidyl acrylate, a glycidyl methacrylate, an alkylene oxide or an epihalohydrin.

7. A process as described in claim 1 wherein the epoxide-containing compound is a polyepoxide having an epoxy equivalent weight of 100 to 1000.

8. A process as described in claim 1 wherein 75 to 100 percent of all hydroxyl groups in the aliphatic hydroxyl-containing compound are primary aliphatic hydroxyl groups.

9. A process as described in claim 1 wherein about 100 percent of all hydroxyl groups in the aliphatic hydroxyl-containing compound are primary aliphatic hydroxyl groups.

10. The process as described in claim 1, wherein "Z" is an organo silyl moiety with the following formula:

wherein "R'" is a hydrogen atom or an organic group.

11. The process as described in claim 10, wherein "R'" is an organic group.

12. The process as described in claim 11, wherein "R'" is an organic group selected from an aliphatic or aromatic group.

13. The process as described in claim 12, wherein "R'" is an alkyl group having from 1 to 20 carbon atoms.

14. The process as described in claim 1, wherein the catalyst is selected from the group consisting of trimethylsilyl trifluoromethylsulfonate, triethylsilyl trifluoromethylsulfonate, triisopropylsilyl trifluoromethylsulfonate, t-butyldiphenylsilyl trifluoromethylsulfonate, t-butyldimethylsilyl trifluoromethylsulfonate, and resins containing pendant moieties of such catalysts.

* * * * *